US005110981A

United States Patent [19]

Milstein

[11] Patent Number: 5,110,981

[45] Date of Patent: May 5, 1992

[54] PROCESS FOR MAKING ALKYL NAPHTHALENE SULFONATE SURFACTANTS

[75] Inventor: Norman Milstein, Montgomery, Ohio

[73] Assignee: Henkel Corporation, Ambler, Pa.

[21] Appl. No.: 717,131

[22] Filed: Jun. 18, 1991

[51] Int. Cl.[5] .......... C07C 61/00

[52] U.S. Cl. .......... 562/90

[58] Field of Search .......... 562/90

[56] References Cited

U.S. PATENT DOCUMENTS

| | | | |
|---|---|---|---|
| 2,422,926 | 6/1947 | Reeves | 562/90 |
| 3,338,983 | 8/1967 | Thompson | 562/90 |
| 3,957,859 | 5/1976 | Thielcke | 562/90 |
| 4,180,521 | 12/1979 | Behre et al. | 562/90 |

*Primary Examiner*—Jose G. Dees
*Assistant Examiner*—Keith MacMillan
*Attorney, Agent, or Firm*—Ernest G. Szoke; Wayne C. Jaeschke; Norvell E. Wisdom, Jr.

[57] ABSTRACT

Incremental alternating additions of sulfonating agent acids and alkylating alcohols give superior results in the synthesis of alkyl naphthalene sulfonate surfactant products from naphthalene starting material.

20 Claims, No Drawings

PROCESS FOR MAKING ALKYL NAPHTHALENE SULFONATE SURFACTANTS

BACKGROUND OF THE INVENTION

1. Field of the Invention

This invention relates to improved processes for making the products commonly known in commerce as "alkyl naphthalene sulfonates", even though they also may contain unreacted naphthalene, alkyl naphthalenes, and molecules with more than one alkyl group and/or sulfonate group per naphthalene molecule. The products are commercially important surfactants, particularly for agricultural use, and are normally made by reacting naphthalene with alcohols, sulfuric acid, and oleum.

2. Statement of Related Art

Butyl naphthalene sulfonate is now commercially made by reacting naphthalene, normal butanol, concentrated sulfuric acid, and oleum in a one-step batch type process. The process normally experiences a vigorous exotherm that is difficult to control and produces large amounts of sulfur containing by-products. On the other hand, isopropyl naphthalene sulfonate is now commercially made by a two-step process, with sulfonation followed by alkylation. While easier to control than the one step process, this two-step process is notably slower and also consumes more acid for by-products than is desirable. Similar situations prevail for other alkyl naphthalene sulfonate products.

After any of these syntheses, the initially formed alkyl naphthalene sulfonic acid is usually converted to the desired surfactant by dissolution in aqueous alkali to convert the acid to a salt. The surfactant may be used directly in the aqueous solution thus formed, or the solution may be dried to produce solid surfactant.

A material known in the art as "free oil" is a common but undesirable constituent of commercial alkyl naphthalene sulfonates. This material is largely unreacted naphthalene and/or unsulfonated alkyl naphthalene(s), and it is common commercial practice to impose an upper limit on the amount of free oil that is acceptable in the product. Another common and undesirable constituent of commercial alkyl naphthalene sulfonates is sulfate salts, formed during neutralization from residual sulfuric acid in the initial reaction product. Limiting the amounts of both these constituents is therefore a desirable goal of any process for making alkyl naphthalene sulfonate surfactants.

It is an object of this invention to provide a process for making alkyl naphthalene sulfonates that avoids or reduces at least some of the difficulties and/or by-products occurring with present commercial processes.

DESCRIPTION OF THE INVENTION

In this description, except in the working examples and claims and wherever expressly indicated to the contrary, all numerical specifications of amounts of materials or conditions of reaction or use are to be understood as modified by the term "about" in describing the broadest scope of the invention. Practice of the invention within the exact numerical limits given is generally preferred.

SUMMARY OF THE INVENTION

It has been found that two major changes from prior art practice greatly improve processes for making alkyl naphthalene sulfonates, particularly those with alkyl groups containing from 1 to 4 carbon atoms. One of these changes is that sulfuric acid and/or oleum and alcohols that contain the alkyl groups desired in the product are added to liquid naphthalene intermittently in small increments, at least at the beginning of the process. Each increment is not more than 10%, more preferably not more than 5%, or still more preferably not more than 2.5% of the amount of the reagent concerned that would be sufficient for complete reaction to the extent desired for the product. The second major novel feature of a process according to this invention is that at an intermediate stage in the reaction, an acid rich second liquid phase is separated from the organic rich first phase, in order to avoid wasting much of the subsequently added sulfuric acid and oleum by its dissolution in the second liquid phase, rather than sulfonating remaining unsulfonated naphthalene and/or alkyl naphthalene(s) in the other liquid phase as desired.

DESCRIPTION OF PREFERRED EMBODIMENTS

A very important practical consideration in processes according to the invention is to maintain reaction conditions, at all times before the final neutralization, that are sufficiently acidic, when alcohol is added to the reaction mixture as alkylating agent, to avoid the formation of substantial amounts of gaseous olefins, which can easily result from dehydration of the alcohols in the presence of some, but not enough, acid. For reasons of both safety and economy, it is preferred that the acidity of the reaction mixture be maintained sufficiently high that the concentration of flammable hydrocarbon vapor in the atmosphere above the predominantly liquid reaction mixture is not more than 100, or with increasing preference, not more than 30, 19, or 8 parts per million by weight ("ppm"). This amount of acid also generally is adequate to catalyze the alkylation reaction sufficiently to achieve a practical reaction rate. However, it has been found that a small amount of alcohol, comparable in size to the increments to be added later, can be added to the naphthalene before addition of any acid, without causing any difficulty from forming byproduct olefin.

The size of the increments used and the time between successive additions of increments of reagents may be varied within wide limits. It is usual to use increments of equal size for the same reagent during at least the part of the process before the liquid-liquid separation stage considered further below, but this is merely a matter of convenience and not a necessary feature of the process. Small increments in general give the best product quality but tend to increase the total reaction time.

With respect to the timing of addition of successive increments, one generally preferred choice is to add the increments whenever the temperature of the reaction mixture falls below a preset limit. The reaction is exothermic overall, at least during most of the reaction sequence, so that each addition of an increment of reagent tends to raise the temperature of the reaction mixture, even when the reaction is performed as preferred in containers with jackets through which heat transfer fluid is circulated or other means for cooling and heating when needed or desired. The timing of addition of increments can conveniently be controlled, either by automatically controlled equipment or from experience, so as to minimize the need for external energy to maintain constant reaction temperature within ±5 degrees Centigrade, as is generally preferred.

The preferred temperature for a process according to this invention varies somewhat with the alkylating agent used. Although an unreactive solvent could be used, it is generally strongly preferred to avoid such a solvent, and in order to have a liquid form of naphthalene as is strongly preferred, this requires a minimum temperature of 80° C., the melting point of naphthalene. The lower that the temperature can be maintained above this practical limit, the less likely is the development of undesirable colored byproducts that reduce the commercial value and/or acceptability of the eventual products. On the other hand, with some alkylating agents such as normal butanol, the reaction is too slow to be practical below about 110° C. For isopropyl alcohol and secondary butyl alcohol, two preferred alkylating agents, an operating temperature between 80 and 90, or more preferably between 83 and 87, degrees Centigrade is preferred.

The strength of the oleum to be used and the proportions of oleum and sulfuric acid to be used in a process according to this invention also may be varied within wide limits, but generally the proportion between oleum and sulfuric acid found useful in the prior art will also be useful for a process according to this invention. It is generally preferred to use enough total sulfonating agent by the end of the process to obtain an average of at least one sulfur atom per naphthalene nucleus in the product, but because of the equilibrium character of the sulfonation reaction, readily detectable amounts of unsulfonated naphthalene nuclei generally remain as part of the "free oil" component mentioned earlier. Some naphthalene nuclei with two or more sulfonate groups are also presumed to be present, although no exhaustive analysis of the products of a process according to this invention has been made.

The amount of alkylating agent used during the complete process also generally should preferably be sufficient to produce a product with an average of at least one alkyl group per naphthalene nucleus. For the alkyl groups, especially butyl, it is still more preferred to have an average of at least 1.1 or still more preferably 1.2 alkyl groups per naphthalene nucleus in the final product. Although it is normally preferred to use an alkylating agent that consists primarily of a single molecular type of alcohol, mixtures of alcohols work effectively in the process as well.

The liquid reaction mixture initially appears homogeneous, but after reaction begins the amount of water produced by reaction eventually becomes sufficient to cause a second liquid phase to appear if agitation of the reaction mixture is stopped for a sufficiently long time; generally a few minutes is sufficient. (During actual reaction, sufficient agitation to achieve vigorous mixing is strongly preferred, in view of the exothermicity of the reaction, to avoid localized "hot spots" that promote the formation of undesired byproducts.) Once this second liquid phase is formed, it competes effectively with the organic phase for newly added sulfuric acid and oleum, and the sulfuric acid and oleum in the second phase are expected to be much less effective in sulfonating than when they are in the same phase as the organic molecules to be sulfonated. Thus, one important factor in the success of a process according to this invention is the separation of this second, sulfuric acid rich phase at some point before the reaction is completed. Preferably the separation is made no later than when five-sixths of the naphthalene nuclei in the reaction mixture have one or more sulfonic groups bonded to them, or more preferably no later than when three-fourths of the nuclei have such substituents. The actual separation may be accomplished by any convenient method for separating two immiscible liquids of different density; many such methods are known in the art. It is generally preferred to cool the mixture during separation to a temperature somewhat lower than that used for reaction, e.g., to 65-70 degrees C.

Before the separation, it is often preferred, although not a necessary part of a process according to this invention, to continue to maintain the reaction mixture at a temperature above 82, or more preferably above 87, degrees Centigrade for a period of at least one-half, more preferably at least two, hours while continuing to agitate the reagent and product mixture, to promote additional sulfonation reactions with the sulfonating agents already present and reduce the eventual free oil content in the product.

After the separation has been accomplished, additional amounts of sulfuric acid, oleum, or both are added to the liquid phase that contains still unsulfonated naphthalene nuclei. Eventually, a sufficient amount of sulfonating agent to achieve an average degree of sulfonation of at least one bonded sulfur atom per naphthalene nucleus and to reduce the amount of free oil in the final product to not more than 1.5% should be used. If the reaction product at the time of the separation from the second liquid phase has a lower average degree of alkylation than is desired for the final product, more alkylating agent may also be added after this phase separation. As is true during the earlier phases of reaction, it is preferable during this phase of reaction to add sulfonating agent and alkylating agent in small increments, with alternating additions of sulfonating agent and of alkylating agent as long as both such reagents are needed to achieve the desired degree of alkylation and sulfonation for the final product, and to time such additions so as to maintain a nearly constant temperature within the reaction mixture.

Additional separations of aqueous second phase from the primary reaction mixture may be made during these final stages of a process according to this invention. If needed, in order to reduce the non-surfactant salt content of the final product, additional water may be added to the mixture of reagents and products in order to assure formation of a second liquid phase and thereby reduce the amount of unreacted sulfuric acid remaining in the organic phase after such a separation.

After all the reagents needed have been mixed together, it is often preferred, even though not a necessary step in a process according to the invention, to continue to maintain the reaction mixture at a temperature above 82, or more preferably above 87, degrees Centigrade for a period of at least one half, more preferably at least two, hours to promote additional sulfonation reactions and reduce the free oil content.

After the completion of the sulfonation and alkylation reactions, the liquid phase containing the products is dissolved in and/or reacted with an alkaline aqueous solution, additional alkali is added if necessary, and the final desired alkyl naphthalene sulfonate surfactants are recovered for use, either as aqueous solutions or in solid form after drying. These final steps are performed in the same general manner as for corresponding steps in the prior art.

In accordance with the discussion above, a process according to the invention comprises steps of:

(A) mixing a specified mass of liquid naphthalene with a first incremental mass of liquid acid selected from the group consisting of sulfuric acid and oleum, said first incremental mass being not more than a specified first proper fraction of the amount sufficient to sulfonate the specified mass of naphthalene with one sulfonate group per naphthalene molecule;

(B) mixing with the mixture formed in step (A) a second incremental mass of alkylating alcohols, said second incremental mass being not more than a specified second proper fraction of the amount sufficient to alkylate the specified mass of naphthalene with one alkyl group per naphthalene molecule and also being small enough that the concentration of gaseous hydrocarbon formed by dehydration of the alkylating alcohols to olefin during mixing does not exceed 100 ppm in the gas phase above the reaction mixture;

(C) mixing with the mixture formed in the previous step a third incremental mass of liquid acid selected from the group consisting of sulfuric acid and oleum, said third incremental mass being not more than a specified third proper fraction of the amount sufficient to sulfonate the specified mass of naphthalene with one sulfonate group per naphthalene molecule;

(D) mixing with the mixture formed in the previous step a fourth incremental mass of alkylating alcohols, said fourth incremental mass being not more than a specified fourth proper fraction of the amount sufficient to alkylate the specified mass of naphthalene with one alkyl group per naphthalene molecule and also being small enough that the concentration of gaseous hydrocarbon formed by dehydration of the alkylating alcohols to olefin during the mixing does not exceed 100 ppm in the gas phase over the reaction mixture;

(E) repeating steps (C) and (D) sufficiently many times that when mixing is discontinued after the last repetition of step (D), the resulting liquid mixture spontaneously separates into two liquid phases, the second, denser, aqueous one of said phases being more concentrated in sulfuric acid than the other phase and the other, first, organic one of said phases being more concentrated in total organic materials than the aqueous second phase; the total amount of liquid acid used in all of steps (A)-(D) and all repetitions of steps (C) and (D) being less than the amount required to sulfonate the specified mass of naphthalene with at least one sulfonate group per naphthalene molecule;

(F) separating the organic phase recited in part (E) from the aqueous phase recited therein;

(G) mixing with the organic phase separated in part (E) a fifth incremental mass of liquid acid selected from the group consisting of sulfuric acid and oleum, said fifth incremental mass being not more than a specified fifth proper fraction of the amount sufficient to sulfonate the specified mass of naphthalene with at least one sulfonate group per naphthalene molecule;

(H) if the total amount of alkylating alcohols mixed with the specified mass of naphthalene by the completion of the previous step is not sufficient to alkylate all the specified mass of naphthalene with at least one alkyl group per molecule of naphthalene, mixing with the mixture formed in the previous step a sixth incremental mass of alkylating alcohols, said sixth incremental mass being not more than a specified sixth proper fraction of the amount sufficient to alkylate the specified mass of naphthalene with one alkyl group per naphthalene molecule and also being small enough that the concentration of gaseous hydrocarbon formed by dehydration of the alkylating alcohols to olefin during the mixing does not exceed 100 ppm in the gas phase over the reaction mixture;

(I) discontinuing agitation of the reaction mixture, so that the mixture can separate into two or more liquid phases if its contents would exist in the form of two or more liquid phases at equilibrium, and separating the resulting liquid phase that is most concentrated in organic material from the other liquid phases present if any; and (J) dissolving the liquid phase that is most concentrated in organic material from step (I) in water and neutralizing the resulting solution with a strong alkali.

In addition to the other optional steps and preferences already noted above, it should be noted explicitly that steps (G) and (H) as described above can be repeated if needed before performing step (I), and that some alcohol can be added before starting step (A).

While the invention is not to be regarded as limited by any theory, it is believed that the superior results obtained by alternating incremental additions of the sulfonating and alkylating agents may perhaps be explicable as follows: The least desirable organic ingredients in the product mixture are those with either no sulfonate groups or no alkyl groups on individual naphthalene molecules. When large amounts of sulfonating agents are added initially, most of the naphthalene nuclei become sulfonated, thereby reducing the reactivity for subsequent alkylation by the well known deactivating effect of sulfonate substituents on aromatic rings. Higher temperatures must then be used to achieve a practical reaction rate, increasing the danger of byproducts. On the other hand, alcohols will not alkylate naphthalene at all in the absence of some acid to serve as catalyst. When a small amount of acid is used at the start, followed by a small amount of alcohol, most of the acid may be bound to the alcohol by temporary bonds that produce the catalytic electrophilic alkylating species, and thereby temporarily unavailable for sulfonating the rings. Once a particular naphthalene nucleus has been alkylated, it is more reactive to sulfonation than either the residual unsubstituted naphthalene or any sulfonated naphthalene that may be present. Therefore, most of the next added increment of sulfonating agent will sulfonate already alkylated naphthalene molecules, and the amount of undesirable product molecules with only one of the two types of substituents will be minimized.

The practice of the invention may be further appreciated from the following working examples.

EXAMPLE 1

An amount of 317 grams ("g") of molten naphthalene is placed in a 3 liter capacity four necked round bottom flask equipped with an agitator, thermometer, and two pressure equalizing addition funnels. An amount of 246 g of 2-butanol was placed in one of the addition funnels and a mixture of 418 g of sulfuric acid, which in these examples means 98% $H_2SO_4$ in water unless otherwise noted, and 239 g of oleum, which in these examples means anhydrous $H_2SO_4$ containing 4% by weight of dissolved $SO_3$ unless otherwise noted, was placed in the other addition funnels. While maintaining agitation, 10 milliliters ("ml") of the acid mixture was added, followed by 10 ml of the butanol, and successive alternate additions of the same increments of acid and alcohol were added at intervals to maintain the temperature of the reaction mixture at 85° C. without external heating. At the end of this period of alternating additions, which consumed a total of three hours, all of the butanol had been used but 85 g of the acid mixture remained in its dropping funnel. The mixture in the flask was held at 87° C. for two additional hours, with heat supplied as needed from a heating jacket around the flask and agitation continued.

Agitation was then discontinued and heating stopped. After 20 minutes ("min") the contents of the flask had separated into two liquid layers and cooled to a temperature in the range from 65°-70° C. The denser, aqueous phase at the bottom of the flask was then removed from the flask. The remaining contents of the flask were then reheated to 87° C. and the remaining acid from the dropping funnel added to it while maintaining agitation, and the temperature was then maintained, with continuing agitation, at 87° C. for two more hours. Agitation and heating were then discontinued, a lower liquid phase which separated was removed, and the remainder of the flask contents dissolved in water and neutralized with sodium hydroxide to produce a liquid sodium butyl naphthalene sulfonate surfactant product containing 42 percent by weight ("w/o") total solids, 34 w/o active surfactant solids, and 4.5 w/o sodium sulfate. The amount of sodium sulfate is determined by determining the amount of sulfate in an accurately weighed sample by a conventional conductometric titration with standardized barium chloride solution, then converting to sodium sulfate by using the proper stoichiometric factor. The amount of active surfactant is determined by the procedure described immediately below.

Determination of Percent Active Surfactant

Apparatus

1. Volumetric Flasks, 100 mL, 1000 mL.
2. Graduated Cylinders with ground glass joint, 100 mL.
3. Graduated Cylinders, 10 mL, 50 mL, 100 mL
4. Volumetric Pipet, 10 mL.

Reagents

1. Chloroform, HPLC Grade
2. Methylene Blue Stock Solution, 1.0 g methylene blue in 1000 mL of distilled water.
3. Methylene Blue Buffered Indicator, 50.0 g sodium phosphate monobasic in 100 mL distilled water, add 30 mL stock solution and 5.4 mL of concentrated sulfuric acid. Dilute to 1000 mL with distilled water.
4 Methylene Blue, water soluble.
5. Sodium Phosphate Monobasic, A.C.S. Grade.
6. Sulfuric Acid, A.C.S. Grade.
7. Cetyl Dimethylbenzylammonium Chloride Solution, 0.0060 normal, accurately standardized.

Procedure

1. Weigh accurately 1.0 g of sample, to the nearest 0.1 mg, into a 100 mL volumetric flask and add distilled water to the mark. Approximately 2 drops of ethanol may be added if necessary to break the foam produced on dissolving in water.

2. Pipet 10 mL of the sample solution into a 100 mL graduated cylinder with ground glass joint. Add 5 mL of distilled water, 15 mL of methylene blue buffered indicator, and 30 mL of chloroform.

3. Titrate 5 mL of the cetyl dimethylammonium chloride solution. Stopper the graduated cylinder and shake vigorously. Continue to titrate with shaking until both phases have the same color after separating completely.

$$\%\ \text{Active} = \frac{(\text{mL in titration})(\text{normality})(\text{MW}^{*})(100)}{(\text{Sample weight})(10\ \text{mL}/100\ \text{mL})(1000\ \text{mL}/\text{L})}$$

*MW of alkylnaphthalene sulfonates:
Methyl = 284; Isopropyl = 314; Butyl = 326.

EXAMPLE 2

This is the same as Example 1, except that (i) 1-butanol is used instead of 2-butanol and (ii) the reaction temperature is maintained between 05 and 110 degrees C. because the primary alcohol is less reactive than the secondary. Substantially the same product is obtained, with primarily secondary butyl groups substituted on the naphthalene, presumably because terminal carbonium ion intermediates formed from 1-butanol rapidly rearrange to a more stable secondary carbonium ion before reacting with the naphthalene.

EXAMPLE 3

An amount of 243.5 g of molten naphthalene is placed in a 2 liter capacity four necked round bottom flask equipped with an agitator, thermometer, and two pressure equalizing addition funnels. An amount of 188.4 g of isopropanol was placed in one of the addition funnels and a mixture of 276 g of sulfuric acid and 312 g of oleum was placed in the other addition funnels. While maintaining agitation, 15 ml of the alcohol was added, followed by 10 ml of the acid mixture, and successive alternate additions of the same increments of alcohol and acid were added at intervals to maintain the temperature of the reaction mixture at 85° C. without external heating. At the end of this period of alternating additions, which consumed a total of about one hour, all of the isopropanol had been used but 133 ml of the acid mixture remained in its dropping funnel. The mixture in the flask was held at 87° C. for two additional hours, with heat supplied as needed from a heating jacket around the flask and agitation continued.

Agitation was then discontinued and heating stopped. After 30 min the contents of the flask had separated into two liquid layers and cooled to a temperature in the range from 65°-70° C. The denser, aqueous phase at the bottom of the flask was then removed from the flask. The remaining contents of the flask were then reheated to 87° C. and the remaining acid from the dropping funnel added to it while maintaining agitation, and the temperature was then maintained, with continuing agitation, at 87° C. for two more hours. Agitation and heating were then discontinued, and the flask contents were poured into a beaker containing 147 g of water, slowly enough to keep the temperature below 60° C. The contents of the beaker were then transferred to a separatory funnel and allowed to settle overnight. The lower layer of spent acid in the separatory funnel was then discarded; the upper layer was dissolved in water and neutralized with sodium hydroxide to produce a liquid sodium isopropyl naphthalene sulfonate surfactant product containing 49.7 w/o total solids, 44.2 w/o surfactant solids, and 5.47 w/o sodium sulfate.

EXAMPLE 4

An amount of 4700 parts by weight ("PBW") of naphthalene is charged to a stirred reactor vessel with a heat transfer fluid jacket for temperature control, the vessel interior having previously been purged with nitrogen to a pressure of about 0.3 bar over atmospheric pressure. The heat transfer fluid outlet temperature is set to 80° C and agitation is begun until all the naphthalene is melted. An amount of 164 PBW of technical grade 2-butanol is added at a rate to maintain the reactor contents temperature in the range from 81°-85° C. Then 270 PBW of sulfuric acid and 150 PBW of oleum are added in succession while maintaining the same temperature.

Additions of the same amounts of 2-butanol, sulfuric acid, and oleum as specified above are repeated in the same order until a total of 3277 PBW of 2-butanol, 5276 PBW of sulfuric acid, and 2953 PBW of oleum have been added, with agitation being continually maintained; the last increment may be smaller than the others, if it represents the entire remaining amount from this total. Then the mixture in the reactor is heated to 85° C. and held there for one hour, then heated to 95° C. and held there for one hour, with agitation continuing throughout this time. Agitation is then discontinued and the mixture is allowed to stand for 5 hours with the heat transfer fluid jacket outlet temperature maintained at 80° C. The mixture separates during this time into two phases. After 5 hours, the bottom phase is removed. The mixture is then allowed to stand for one additional hour at the same temperature, to determine whether any additional lower phase will form. If more lower phase does form, it is removed after one hour.

The reactor contents are then agitated for 10 min, and a sample is taken from the reactor contents. Free oil, percent total solids, and sodium sulfate contents are then determined for the sample. Sodium sulfate is determined by the method already given above; percent total solids is determined by drying an accurately weighed sample and calculating the percent of residue after drying in the sample before drying; and the free oil is determined by the following method:

Determination of Free Oil

Apparatus and Reagents

Separatory funnels, 2, 500 mL
Beakers, 2, 250 mL
Balance, analytical
Ring Stand, clamps
Petroleum Ether
Isopropyl Alcohol
Magnetic Stirrer and Magnetic Stirring Bar
Desiccator (with silica gel desiccant)
Steam Bath or Table
Boiling Stones

Procedure

1. Accurately weigh 30±0.1 g of alkyl naphthalene sulfate solution into tared 250 mL beaker.
2. Add a solution of 1:1 isopropyl alcohol/distilled water to the 100 mL mark.
3. Mix on magnetic stirrer for one minute to effect complete solution.
4. Add stirred contents to the upper of two separatory funnels set up in series, one above the other, on ring stand.
5. Rinse beaker with 50 mL of the 1:1 isopropyl alcohol solution and add to first funnel.
6. Add 50 mL of petroleum ether to beaker, stir.
7. Add this petroleum ether to upper separatory funnel.
8. Shake vigorously for one minute after venting to release pressure. NOTE: Care must be taken to vent pressure by inverting funnel and slowly opening stop cock. Repeat this procedure after each agitation, until no pressure is evident.
9. Allow to settle till complete separation of two phases occurs.
10. Draw lower phase from upper funnel into lower funnel until about 5 mL of the lower phase remains in the upper funnel.
11. Swirl contents of upper funnel, approximately 3 or 4 swirls, then allow to settle about one minute.
12. Drop off the lower layer until the interface is at the stop cock, stop. Then turn the stop cock quickly 180°, twice.
13. Drop remaining petroleum extract from the upper funnel into a tared 250 mL beaker containing two boiling stones.
14. Interchange the two funnels by placing the lower funnel, containing the solution under analysis, on the top ring and the previously upper funnel on the bottom.
15. Add 50 mL of petroleum ether to the upper funnel.
16. Repeat Steps 8, 9, 10, 11, 12, 13 and 14.
17. Add an additional 50 mL of petroleum ether and repeat Step 16. (This will have created a total of three extracts).
18. Place all three extracts in the 250 mL beaker on the steam bath.
19. Leave on steam bath until approximately ten minutes past the last noticeable bubbling of the solvent.
20. Dry the bottom of the beaker and place in a desiccator for one hour.
21. Weigh the beaker after drying, deduct the tare weight to give the residue weight, and calculate the free oil:

$$(100)\frac{\text{Residue weight}}{\text{Sample weight}} = \%\ \text{Free oil}$$

An amount $W_o$ of oleum to be added is determined by calculation as follows:

$$W_o=(W_t)\{[(\%_{fo}-1.0)/\%_s](98/M_{an})+[(6.8-\%_{ss})/\%_s](98/142)\},$$

where $W_t$ represents the total weight of crude partial reaction product sampled, to which the oleum will be added; $\%_{fo}$ represents percent free oil in the sample, $\%_s$ represents percent total solids in the sample; $M_{an}$ represents the molecular weight of a monoalkyl naphthalene with the alkylating agent used, in this case 184 for butyl naphthalene; and $\%_{ss}$ represents the percent sodium sulfate in the sample.

After addition of this amounts of post phase separation oleum, the additions being performed over a period of about 30 min with agitation, the mixture is held with continued agitation at 85°-90° C. for 2 hours, then cooled to 50°-60° C. An amount of 8000 PBW of water is then added to the reactor contents at a rate so as to maintain the contents at a temperature in the range from 70°-80° C. Addition of an amount of 4300 PBW of 50% aqueous sodium hydroxide solution is then begun and continued at a rate to maintain the temperature as before. Additional sodium hydroxide is then added to the extent necessary to bring the pH value of the reactor contents to 9.5. Finally, additional water may be added if desired, to achieve a particular solids value for the butyl naphthalene sulfonate product.

What is claimed is:

1. A process for making surfactant material, said process comprising steps of:

(A) mixing a specified mass of liquid naphthalene with a first incremental mass of liquid acid selected from the group consisting of sulfuric acid and oleum, said first incremental mass being not more than a specified first proper fraction of the amount sufficient to sulfonate the specified mass of naphthalene with one sulfonate group per naphthalene molecule;

(B) mixing with the mixture formed in step (A) a second incremental mass of alkylating alcohols, said second incremental mass being not more than a specified second proper fraction of the amount sufficient to alkylate the specified mass of naphthalene with one alkyl group per naphthalene molecule and also being small enough that the concentration of gaseous hydrocarbon formed by dehydration of the alkylating alcohols to olefin during mixing does not exceed about 100 ppm in the gas phase above the reaction mixture;

(C) mixing with the mixture formed in the previous step a third incremental mass of liquid acid selected from the group consisting of sulfuric acid and oleum, said third incremental mass being not more than a specified third proper fraction of the amount sufficient to sulfonate the specified mass of naphthalene with one sulfonate group per naphthalene molecule;

(D) mixing with the mixture formed in the previous step a fourth incremental mass of alkylating alcohols, said fourth incremental mass being not more than a specified fourth proper fraction of the amount sufficient to alkylate the specified mass of naphthalene with one alkyl group per naphthalene molecule and also being small enough that the concentration of gaseous hydrocarbon formed by dehydration of the alkylating alcohols to olefin during the mixing does not exceed about 100 ppm in the gas phase over the reaction mixture;

(E) repeating steps (C) and (D) sufficiently many times that when mixing is discontinued after the last repetition of step (D), the resulting liquid mixture spontaneously separates into two liquid phases, the second, denser, aqueous one of said phases being more concentrated in sulfuric acid than the other phase and the other, first, organic one of said phases being more concentrated in total organic materials than the aqueous second phase; the total amount of liquid acid used in all of steps (A)-(D) and all repetitions of steps (C) and (D) being less than the amount required to sulfonate the specified mass of naphthalene with at least one sulfonate group per naphthalene molecule;

(F) separating the organic phase recited in part (E) from the aqueous phase recited therein;

(G) mixing with the organic phase separated in part (E) a fifth incremental mass of liquid acid selected from the group consisting of sulfuric acid and oleum, said fifth incremental mass being not more than a specified fifth proper fraction of the amount sufficient to sulfonate the specified mass of naphthalene with at least one sulfonate group per naphthalene molecule;

(H) if the total amount of alkylating alcohols mixed with the specified mass of naphthalene by the completion of the previous step is not sufficient to alkylate all the specified mass of naphthalene with at least one alkyl group per molecule of naphthalene, mixing with the mixture formed in the previous step a sixth incremental mass of alkylating alcohols, said sixth incremental mass being not more than a specified sixth proper fraction of the amount sufficient to alkylate the specified mass of naphthalene with one alkyl group per naphthalene molecule and also being small enough that the concentration of gaseous hydrocarbon formed by dehydration of the alkylating alcohols to olefin during the mixing does not exceed about 100 ppm in the gas phase over the reaction mixture;

(I) discontinuing agitation of the reaction mixture, so that the mixture can separate into two or more liquid phases if its contents would exist in the form of two or more liquid phases at equilibrium, and separating the resulting liquid phase that is most concentrated in organic material from the other liquid phases present if any; and (J) dissolving the liquid phase that is most concentrated in organic material from step (I) in water and neutralizing the resulting solution with a strong alkali.

2. A process according to claim 1, comprising an additional step (E') between steps (E) and (F), said additional step consisting of heating the mixture formed after all previous additions of liquid acid and alkylating alcohols, with mixing, so as to maintain the mixture at a temperature of at least about 85° C. for a time period of at least about 30 minutes.

3. A process according to claim 2, comprising an additional step (H') between steps (H) and (I), said additional step being selected from the group consisting of (i) heating the mixture formed after all additions of liquid acid and alkylating alcohols with mixing so as to maintain at temperature of at least about 85° C. within the mixture for a time period of at least about 30 minutes; (ii) mixing with the mixture formed after all additions of liquid acid and alkylating alcohols an amount of water large enough that the resulting mixture will exist in two or more liquid phases at equilibrium; and (iii) first heating the mixture formed after all additions of liquid acid and alkylating alcohols with continued mechanical agitation so as to maintain at temperature of at least about 85° C. within the mixture for a time period of at least about 30 minutes and then mixing with the resulting heated mixture an amount of water large enough that the resulting mixture will exist in two or more liquid phases at equilibrium.

4. A process according to claim 2, wherein the total amount of liquid acid added by the beginning of step (F) is not more than about three-quarters of the total amount sufficient to sulfonate all the specified mass of naphthalene with at least one sulfonate group per molecule of naphthalene.

5. A process according to claim 2, wherein the amount of alkylating alcohols added by the end of step (I) is sufficient to alkylate each molecule of naphthalene in the specified mass of naphthalene with an average of at least about 1.2 alkyl groups per molecule of naphthalene.

6. A process according to claim 5, wherein each of said first through fourth proper fractions is not more than about 0.05.

7. A process according to claim 4, wherein each of said first through fourth proper fractions is not more than about 0.05.

8. A process according to claim 3, wherein each of said first through fourth proper fractions is not more than about 0.1.

9. A process according to claim 2, wherein each of said first through fourth proper fractions is not more than about 0.1.

10. A process according to claim 1, wherein each of said first through fourth proper fractions is not more than about 0.1.

11. A process according to claim 10, wherein said alkylating alcohols are selected from the group consisting of 2-propanol and 2-butanol and the temperature during steps (A) -(H) is maintained within the range from about 82° - about 87° C.

12. A process according to claim 9, wherein said alkylating alcohols are selected from the group consisting of 2-propanol and 2-butanol and the temperature during steps (A) -(H) is maintained within the range from about 82° - about 87° C.

13. A process according to claim 8, wherein said alkylating alcohols are selected from the group consisting of 2-propanol and 2-butanol and the temperature during steps (A) (H) is maintained within the range from about 82° - about 87° C.

14. A process according to claim 7, wherein said alkylating alcohols are selected from the group consisting of 2-propanol and 2-butanol and the temperature during steps (A) -(H) is maintained within the range from about 82° - about 87° C.

15. A process according to claim 6, wherein said alkylating alcohols are selected from the group consisting of 2-propanol and 2-butanol and the temperature during steps (A) -(H) is maintained within the range from about 82° - about 87° C.

16. A process according to claim 5, wherein said alkylating alcohols are selected from the group consisting of 2-propanol and 2-butanol and the temperature during steps (A) -(H) is maintained within the range from about 82° - about 87° C.

17. A process according to claim 4, wherein said alkylating alcohols are selected from the group consisting of 2-propanol and 2-butanol and the temperature during steps (A) -(H) is maintained within the range from about 82° - about 87° C.

18. A process according to claim 3, wherein said alkylating alcohols are selected from the group consisting of 2-propanol and 2-butanol and the temperature during steps (A) -(H) is maintained within the range from about 82° - about 87° C.

19. A process according to claim 2, wherein said alkylating alcohols are selected from the group consisting of 2-propanol and 2-butanol and the temperature during steps (A) -(H) is maintained within the range from about 82° - about 87° C.

20. A process according to claim 1, wherein said alkylating alcohols are selected from the group consisting of 2-propanol and 2-butanol and the temperature during steps (A) -(H) is maintained within the range from about 82° - about 87° C.

* * * * *

UNITED STATES PATENT AND TRADEMARK OFFICE

CERTIFICATE OF CORRECTION

PATENT NO. : 5,110,981

DATED : May 05, 1992

INVENTOR(S) : Milstein, N.

It is certified that error appears in the above-identified patent and that said Letters Patent is hereby corrected as shown below:

In claim 13, column 13, line 28, "(A) (H)" should read --(A)-(H)--.

Signed and Sealed this

Seventh Day of September, 1993

*Attest:*

BRUCE LEHMAN

*Attesting Officer*

*Commissioner of Patents and Trademarks*